(12) United States Patent
Khosroshahi

(10) Patent No.: US 10,883,923 B2
(45) Date of Patent: Jan. 5, 2021

(54) EARLY CANCER BIOMARKER DETECTION USING COMBINED NANOPARTICLE-OPTICAL FIBRE, TUNABLE OPTICAL HETRODYNING, FLUORESCENCE AND SENSOR SYSTEM

(71) Applicant: M.I.S. Electronics Inc., Richmond Hills (CA)

(72) Inventor: Mohammad E Khosroshahi, Richmond Hill (CA)

(73) Assignee: M.I.S. Electronics Inc., Richmond Hill (CA)

( * ) Notice: Subject to any disclaimer, the term of this patent is extended or adjusted under 35 U.S.C. 154(b) by 161 days.

(21) Appl. No.: 15/996,011

(22) Filed: Jun. 1, 2018

(65) Prior Publication Data

US 2018/0348118 A1 Dec. 6, 2018

Related U.S. Application Data

(60) Provisional application No. 62/513,648, filed on Jun. 1, 2017.

(51) Int. Cl.
| | |
|---|---|
| *G01N 21/17* | (2006.01) |
| *G01N 33/49* | (2006.01) |
| *G01N 21/64* | (2006.01) |
| *G01N 33/543* | (2006.01) |
| *G01N 29/46* | (2006.01) |
| *G01L 1/24* | (2006.01) |
| *G01N 33/553* | (2006.01) |
| *G01N 29/24* | (2006.01) |

(52) U.S. Cl.
CPC .......... *G01N 21/1702* (2013.01); *G01L 1/245* (2013.01); *G01N 21/6402* (2013.01); *G01N 21/6486* (2013.01); *G01N 29/2418* (2013.01); *G01N 29/46* (2013.01); *G01N 33/49* (2013.01); *G01N 33/543* (2013.01); *G01N 33/54373* (2013.01); *G01N 33/553* (2013.01); *G01N 2021/1706* (2013.01); *G01N 2021/1761* (2013.01); *G01N 2021/6484* (2013.01); *G01N 2291/0255* (2013.01)

(58) Field of Classification Search
None
See application file for complete search history.

(56) References Cited

U.S. PATENT DOCUMENTS

| | | | | |
|---|---|---|---|---|
| 2006/0045809 A1* | 3/2006 | Shirai | ............... | G01N 33/54373 422/82.11 |
| 2013/0260479 A1* | 10/2013 | Chou | ................... | G01N 21/648 436/501 |
| 2014/0200240 A1* | 7/2014 | Gabriel | ................ | G01N 33/86 514/301 |

* cited by examiner

*Primary Examiner* — Melanie Brown
*Assistant Examiner* — Richard Moerschell
(74) *Attorney, Agent, or Firm* — Elan IP Inc.

(57) ABSTRACT

This invention relates a biomarker detection system, for detecting cancer biomarkers using optical heterodyning. The system includes a tunable laser configured to produce a plurality of laser beams of at least two frequencies, a pair of optical fibers coated with gold nanoparticles and functionalized with an antibody is configured to undergo a change of fiber surface of each optical fiber by adsorbing molecules of an analyte on a surface of the antibody, modify a reflection of the plurality of laser beams inside a fiber core of the each optical fiber when the each optical fiber is bent, and create an audible beat frequency; and perform spectral analysis. A frequency spectrum analyzer configured to provide a composition information of the adsorbed molecules based on a spectral analysis of the beat frequency.

9 Claims, 3 Drawing Sheets

EARLY CANCER BIOMARKER DETECTION USING COMBINED NANOPARTICLE-OPTICAL FIBRE, TUNABLE OPTICAL HETRODYNING, FLUORESCENCE AND SENSOR SYSTEM

(1) FIELD OF THE INVENTION

The present invention generally relates to the field of cancer biomarker detection. The present invention, particularly relates to cancer biomarker detection using antibody conjugated nanoparticles, tunable optical heterodyning and fluorescence system.

(2) BACKGROUND OF THE INVENTION

Early detection of oncological pathology is critical to diagnosis and effective treatment of pathological conditions such as cancer. Typically detection of cancer biomarkers in a human body indicates presence of cancer in such human body. Analyzing and monitoring molecular, biochemical, physiological features of such cancer biomarkers enable assessment of the disease and thereby predict an effective treatment.

Various techniques are used in prior art for early detection of oncological pathology, such as surface enhanced Raman scattering, optical spectroscopy and use of gold nanoparticles for protein corona studies. For example, the following patents are provided for their supportive teachings and are all incorporated by reference: Non-patent literature prior art document, "Visible-absorption spectroscopy as a biomarker to predict treatment response and prognosis of surgically resected esophageal cancer", by Pei-Wen Yang et al. (see: Scientific Reports; Volume 6, Article number: 33414, 2016, https://www.nature.com/articles/srep33414), discloses use of optical spectrum of a tissue to determine information about the structure and the biochemical composition of the tissue in a non-invasive manner and in real-time. Optical spectroscopy is used as a technique in the diagnosis of cancers. The prior art teaches, the region of 600-1000 nm, as the diagnostic and therapeutic window in which scattering predominates over absorption in tissue. However, the accuracy in detection by disclosed prior art is only 78-93%. Further use of a tungsten halogen light source (Ocean Optics, HL2000-HP-FHSA) with a wavelength range from 360 nm to 1700 nm to scan a sample being analyzed, does not ensure high sensitivity when the biomarker concentration is low.

Another prior art document, WO2015140362A1 describes use of a biosensor comprising a metallic substrate on which is implemented at least one nanostructure, wherein said at least one nanostructure is designed to produce localized plasmon resonance surface (LSPR) when subjected to optical radiation. The metal layer with at least one nano structure, is biofunctionalized with at least one biomolecule recognizing at least one biomarker in a sample. However, development of the disclosed biosensor is expensive in construction and use. Further, the working of the biomarker system uses reference system to detect pathological condition; it is not accurate in responding to low concentration biomarkers that are below the standard thresholds.

Another prior art document, US2012129192A describes a detector CTCs based microfluidic system and a set of nanostructures functionalized with antibodies. These nanostructures are nano-needles highly flexible. Detecting CTCs is based on that they are trapped by nano-needles. However, this system cannot be specific. The nano-needles are designed for cells of a certain size become trapped between them. However, the risk of other different cells CTCs, but of similar size (eg blood monocytes) also remains trapped, or CTCs, due to its plasticity, are not trapped run, distorting final score.

Another prior art, is a commercial product—Cell Collector™ of GILUPI (see: http://www.gilupi.com/cellcollector-.html), that detects rare cells, such as circulating tumor cells (CTCs), in vivo. However, though the accuracy in detecting low concentrations CTCs is high, this is an invasive technique that is applied in the hospital while the patient receives his therapy and after it.

Another prior art, is Swee J T et al., Versatile free label biochip for the detection heard circulating tumor cells from peripheral blood in Cancer Patients (see: Biosensors and Bioelectronics, Volume 26, pages 1701-1705, 2010; https://www.ncbi.nlm.nih.gov/pubmed/20719496). This prior art describes the separation of CTCs using a microfluidic device, based on the differences in size and deformability between cancer cells and blood cells. However, this also being an invasive technique is not recommended for pre diagnosis and patients with fragile health conditions.

Accordingly, aforementioned techniques are limited by low sensitivity for low biomarker concentration, three dimensional protein concentration and diverse forms of proteins. For example, micro array chips have shown limitations in detecting very low concentration of biomarker proteins and bioreceptors with sufficiently high affinity. Further, other transduction techniques, despite relatively acceptable sensitivity, are often limited by number of factors such as lack of wide proteins spectra selectivity.

Hence there is a need for an alternate method and system for detecting low concentration of biomarker proteins such as cancer biomarkers. Further, the alternate method and system must show acceptable sensitivity in detecting a wide spectrum of proteins. Accordingly, an alternate method and system for detecting biomarker proteins using optical heterodyning is disclosed.

(3) SUMMARY OF THE INVENTION

In the view of the foregoing disadvantages inherent in the known methods of biomarker detection now present in the prior art, the present invention provides a multi-combined system based on heterodyning frequency shift detection due to protein-antibody conformational changes and continuous monitoring of fluorescence spectrum as well as medium light transmission. As such, the general purpose of the present invention, which will be described subsequently in greater detail, is to provide a dynamical analytical operating system based on simultaneous multi-task information platform acting as cancer biomarker detection system by identifying the presence and type of protein in the biological medium of interest under test such as blood serum, which has all the advantages of the prior art and none of the disadvantages.

An object of the invention is to provide a biomarker detection system, the system comprising: a tunable laser configured to produce a plurality of laser beams of at least two frequencies; a pair of optical fibers coated with gold nanoparticles and functionalized with an antibody is configured to undergo a change of fiber surface of each optical fiber by adsorbing molecules of an analyte on a surface of the antibody; modify a reflection of the plurality of laser beams inside a fiber core of the each optical fiber when the each optical fiber undergoes bending; and create an audible beat frequency; and a frequency spectrum analyzer configured to provide a composition information of the adsorbed molecules based on a spectral analysis of the audible beat frequency.

It is another objective of the present invention is to provide an antibody conjugated gold nanoparticle smart optical fiber sensor in a biomarker detection system that produces a change of heterodyning frequency due to fiber micro bending. A tunable, pulsed and continuous optical source is utilized such that energy and power spectral density is analyzed and essential dynamical information regarding the physical process is achieved and cross-correlated to output signal of optoelectronic sensor. Simultaneously biochemical information such as the presence and type of protein is obtained by laser-induced fluorescence spectroscopy.

It is another object of the invention to provide a biomarker detection system comprising a tunable laser configured to produce a plurality of laser beams of at least two frequencies; a pair of optical fibers coated with gold nanoparticles and functionalized with an antibody to undergo a change of fiber surface of each optical fiber by adsorbing molecules of an analyte on a surface of the antibody; modify a reflection of the plurality of laser beams inside a fiber core of the each optical fiber when the each optical fiber is bent; and create an audible beat frequency; and perform spectral analysis; and a frequency spectrum analyzer configured to provide a composition information of the adsorbed molecules based on a spectral analysis of the beat frequency.

It is another object of the invention to provide a beam expander to receive as input the plurality of laser beams from the tunable laser; and to increase a size of each of the plurality of laser beams.

It is another object of the invention to provide a pair of phototransistors to detect the beat frequency created by the pair of optical fibers; and produce an electric current output equivalent to the beat frequency.

It is another object of the invention to provide an RC circuit to receive the equivalent electric current output; and produce a rectified output voltage; and It is another object of the invention to provide a pair of potentiometers configured to receive the rectified output voltage form the pair of RC circuits.

It is another object of the invention to provide an operational amplifier to produce an output voltage equivalent to a gained difference between the rectified output voltage as received from the pair of potentiometers.

It is another object of the invention to provide a capacitor to receive as input the output voltage from the operational amplifier; and an audio speaker configured to output a sound recording of the output voltage.

It is another object of the invention to provide adsorb an analyte that is present in a biological sample, and wherein the biological sample is blood sample of a human body. In an embodiment, the molecules are at least one of a cancer biomarker and a protein.

It is another object of the invention to provide a pair of bifurcated optical fibers configured to detect fluorescence of the adsorbed molecules; and deliver the fluorescence to a Ultraviolet and visible (UV-Vis) spectrometer.

It is another object of the invention to provide a cadmium-sulfide (CdS) sensor configured to monitor a dynamic change in the plurality of laser beams transmitted through the pair of optical fibers.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

These together with other objects of the invention, along with the various features of novelty which characterize the invention, are pointed out with particularity in the disclosure. For a better understanding of the invention, its operating advantages and the specific objects attained by its uses, reference should be had to the accompanying drawings and descriptive matter in which there are illustrated preferred embodiments of the invention.

(4) BRIEF DESCRIPTION OF THE DRAWINGS

The invention will be better understood and objects other than those set forth above will become apparent when consideration is given to the following detailed description thereof. Such description makes reference to the annexed drawings wherein.

(5) DETAILED DESCRIPTION OF THE INVENTION

Figure 1:
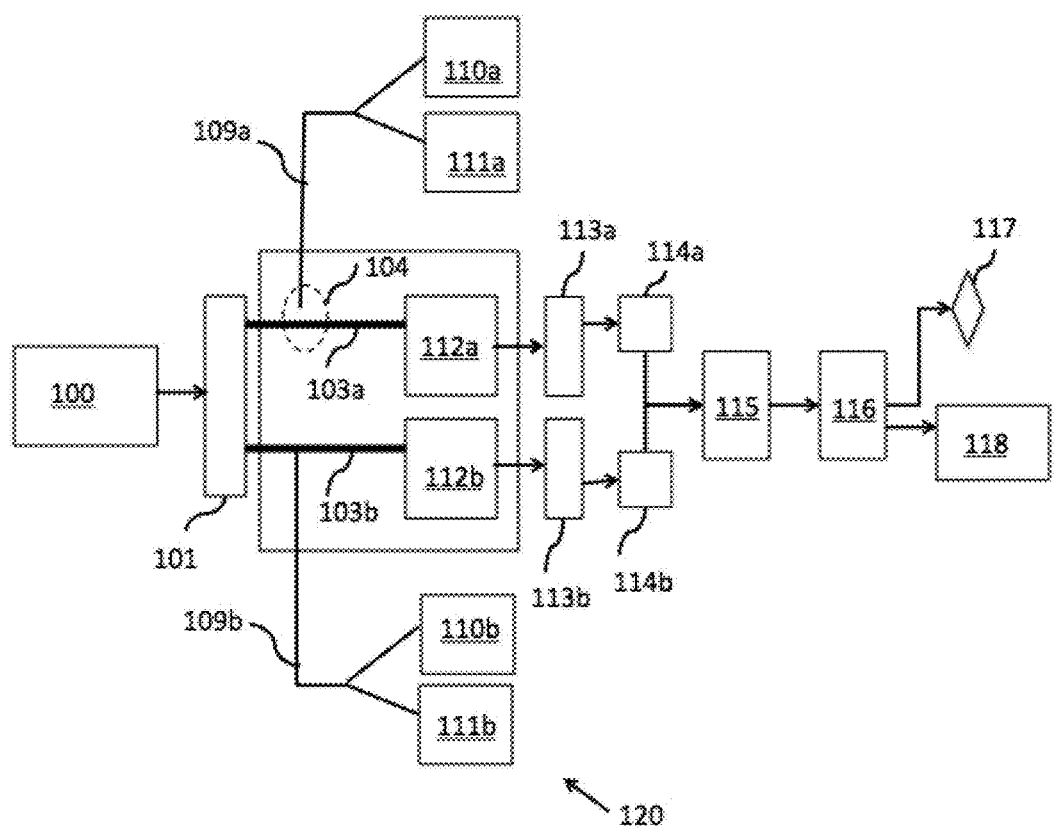
FIG. 1 depicts a block diagram of a biomarker detection system, according to one of the preferred embodiment of the present invention.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural and logical changes may be made without departing from the spirit and scope of the present invention. The following detailed description is, therefore, not to be taken in a limiting sense, and the scope of the present invention is defined by the appended claims and their equivalents.

The present invention is described in brief with reference to the accompanying drawings. Now, refer in more detail to the exemplary drawings for the purposes of illustrating non-limiting embodiments of the present invention.

As used herein, the term "comprising" and its derivatives including "comprises" and "comprise" include each of the stated integers or elements but does not exclude the inclusion of one or more further integers or elements.

As used herein, the singular forms "a", "an", and "the" include plural referents unless the context clearly dictates otherwise. For example, reference to "a device" encompasses a single device as well as two or more devices, and the like.

As used herein, the terms "for example", "like", "such as", or "including" are meant to introduce examples that further clarify more general subject matter. Unless otherwise specified, these examples are provided only as an aid for understanding the applications illustrated in the present disclosure, and are not meant to be limiting in any fashion.

As used herein, the terms "may", "can", "could", or "might" be included or have a characteristic, that particular component or feature is not required to be included or have the characteristic.

Exemplary embodiments will now be described more fully hereinafter with reference to the accompanying drawings, in which exemplary embodiments are shown. These exemplary embodiments are provided only for illustrative purposes and so that this disclosure will be thorough and complete and will fully convey the scope of the invention to those of ordinary skill in the art. The invention disclosed may, however, be embodied in many different forms and should not be construed as limited to the embodiments set forth herein.

Various modifications will be readily apparent to persons skilled in the art. The general principles defined herein may be applied to other embodiments and applications without departing from the spirit and scope of the invention. Moreover, all statements herein reciting embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Thus, for example, it will be appreciated by those of ordinary skill in the art that the diagrams, schematics, illustrations, and the like represent conceptual views or processes illustrating systems and methods embodying this invention. The functions of the various elements shown in the figures may be provided through the use of dedicated hardware as well as hardware capable of executing associated software. Similarly, any switches shown in the figures are conceptual only. Their function may be carried out through the operation of program logic, through dedicated logic, through the interaction of program control and dedicated logic, or even manually, the particular technique being selectable by the entity implementing this invention. Those of ordinary skill in the art further understand that the exemplary hardware, software, processes, methods, and/or operating systems described herein are for illustrative purposes and, thus, are not intended to be limited to any particular named element.

Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Various terms as used herein are shown below. To the extent a term used in a claim is not defined below, it should be given the broadest definition and persons in the pertinent art have given that term as reflected in printed publications and issued patents at the time of filing.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all groups used in the appended claims.

The present invention provides a cancer biomarker detection system that provides a spectral analyses of biomarker compositions that are detected by an embedded optical heterodyning system. The optical heterodyning system consists of a pair of optical fibers and a pair of phototransistors. The pair of optical fibers are typically antibody conjugated gold nanoparticle smart optical fiber sensors that produces a change of heterodyning frequency due to fiber micro bending. Initially, a tunable pulsed and continuous optical source is utilized to provide a plurality of laser beams to pass through the pair of optical fibers. The plurality of laser beams undergoes modification in reflection due to micro bending of each optical fiber. Micro bending occurs when particles of an analyte are adsorbed on a surface of the each optical fiber. In an embodiment, the analyte is a cancer biomarker present within a biological sample such as blood serum. As a result of the modification in reflection, an audible beat frequency is produced within the each optical fiber. The audible beat frequency usually carries information of the composition of the adsorbed molecules on the surface of the each optical fiber. The audible beat frequency is converted into an electrical output voltage using phototransistors, and amplified by an operational amplifier. The output of the operational amplifier is then provided to a frequency spectrum analyzer that provides as spectrum analysis of the electrical voltage. Hence, physical and biochemical information of protein or a cancer biomarker in the analyte is obtained by aforementioned laser-induced fluorescence spectroscopy.

FIG. 1 depicts a block diagram of a biomarker detection system 120 based on optical heterodyning. The biomarker detection system 120 includes a tunable laser 100, a beam expander 101, a heterodyning system, a pair of bifurcated optical fibers 109*a-b*, a pair of optical fibers 103*a-b*, a pair of phototransistors 112*a-b*, a pair of RC circuits 113*a-b*, a pair of potentiometers 114*a-b*, an operational amplifier 115, a capacitor 116, an audio speaker 117, a frequency spectrum analyzer 118, a pair of Ultraviolet and visible (UV-Vis) UV spectrometer 110*a-b*, and a pair of semiconductor cadmium-sulphide (Cds) sensor 111*a-b*.

The tunable laser 100, is a source of optical frequencies. The tunable laser 100 basically operates in two modes viz. pulse and continuous where both the energy spectral density and power spectral density at different wavelengths describe how the energy and power of a signal or time series is distributed with frequency. The beam expander 101 expands the output viz. optical frequency light, of the tunable laser 100. The expanded set of optical frequencies then enter an optical heterodyning system. The optical heterodyning system includes the pair of optical fibers 103a-b, and the pair of phototransistors 112a-b. A section of an optical fiber viz. optical fiber 109a is shown in FIG. 2.

Figure 2:
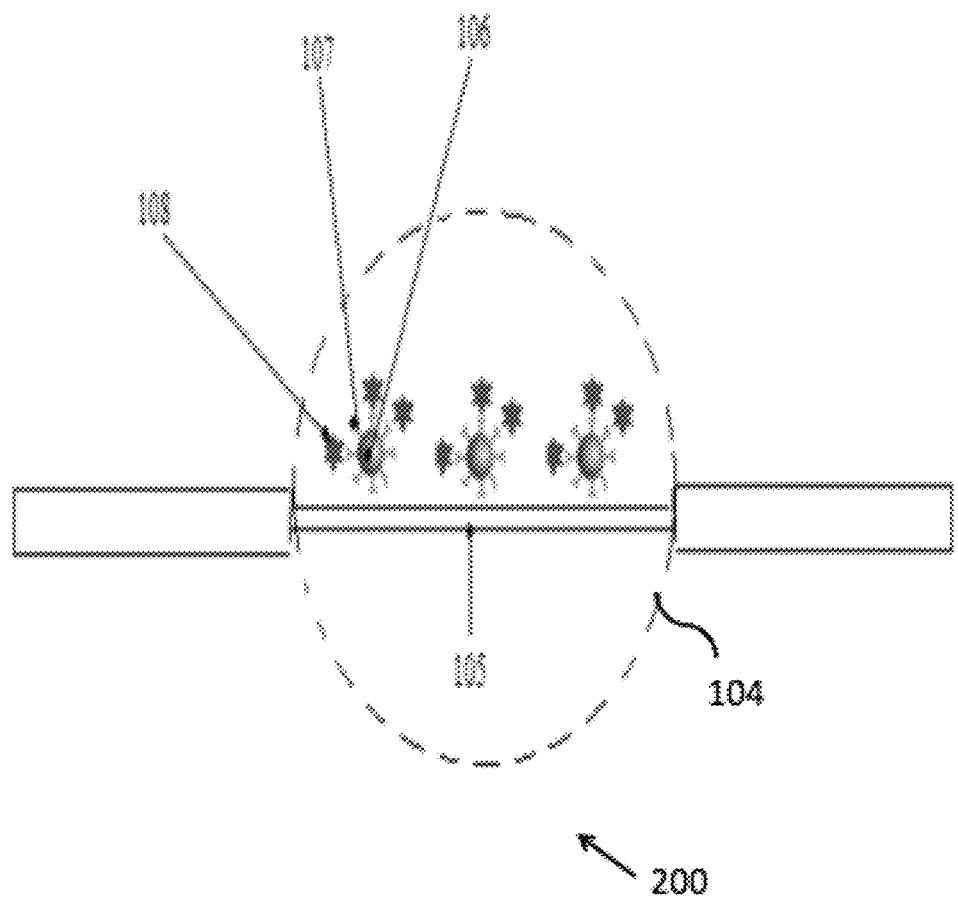
FIG. 2 depicts a an exploded view of a section of an optical fiber sensor used in the biomarker detection system of FIG. 1, according to one of the preferred embodiment of the present invention.

FIG. 2 illustrates an exploded view 200 of a section 104 of the optical fiber 109a. The optical fiber 109a includes a fiber core 105. A surface of the fiber core 105, is coated by gold nanoparticles 106. functionalized by antibody 107. Proteins such protein 108 is adsorbed at a surface of the antibody 107 by 'Vroman's corona effect'. Due to adsorption of the proteins on the surface of the optical fiber 109a as aforementioned, the surface undergoes a dynamical change due to molecular conformational structure. As a result, micro bending of the optical fiber 109a and similarly of the optical fiber 109b occurs. Due to micro bending, the way the laser light reflects inside the optical fibers 113a-b changes which in turn changes the coherency. Further, slow bending or movement of the fiber core 105 also results in audio noise or squeals. Typically, the squeals are caused by Doppler effect of optical heterodyning, a process whereby two beams of light with different frequencies interfere. When two fundamental frequencies mix together, they result in two additional frequencies viz. one is sum of the two frequencies and the other is the difference. The difference is termed as a beat frequency. The sum of the two frequencies is ultrasonic and cannot be heard but the difference frequency also known as the beat frequency is audible and can be detected by the pair of phototransistors 112a-b. Further, the output is fed to the RC circuit 113a-b rectifies the output and feeds it to the pair of potentiometers 114a-b. The output from the pair of potentiometers 114a-b is then fed to the operational amplifier 115 that amplifies an amplitude of the output. The amplified output is further provided to the capacitor 116. The output from the capacitor 116 is fed to both the audio speaker 117 for data recording and the frequency spectrum analyzer 118 for further spectral analysis. Typically, spectrum of a physical or a physiochemical process contains essential information about the nature of an event as a function of time. Hence, information regarding conformation of proteins 108 that are adsorbed on the surface of the antibody 107 present on the surface of the optical fiber 103a is analyzed by the frequency spectrum analyzer 118. For example, dynamical conformation of cancer biomarkers can be determined and analyzed by the optical heterodyning system as described above.

Further, the molecular dynamic changes, which cause a change in the laser light that is transmitted through the optical fiber 109a is monitored by the Ultraviolet and visible (UV-Vis) spectrometer 110a. Similarly, the molecular dynamic changes, which cause a change in the light transmitted through the optical fiber 109b is monitored through the Ultraviolet and visible (UV-Vis) UV spectrometer 110b. Laser-induced fluorescence of proteins that occurs within optical fiber 109a is detected and delivered by the bifurcated optical fiber 109a to the Ultraviolet and visible (UV-Vis) UV spectrometer 110a and the semiconductor Cds sensor 111a. The dynamical change in transmitted light is monitored depending on the conditions. Simultaneous use of laser-induced fluorescence and frequency spectrum analyzer 118 facilitates analyzing composition and dynamic behavior of molecules such as cancer biomarkers. As a result, early detection of cancer and early treatment is achieved by disclosed biomarker detection system 120.

Figure 3:
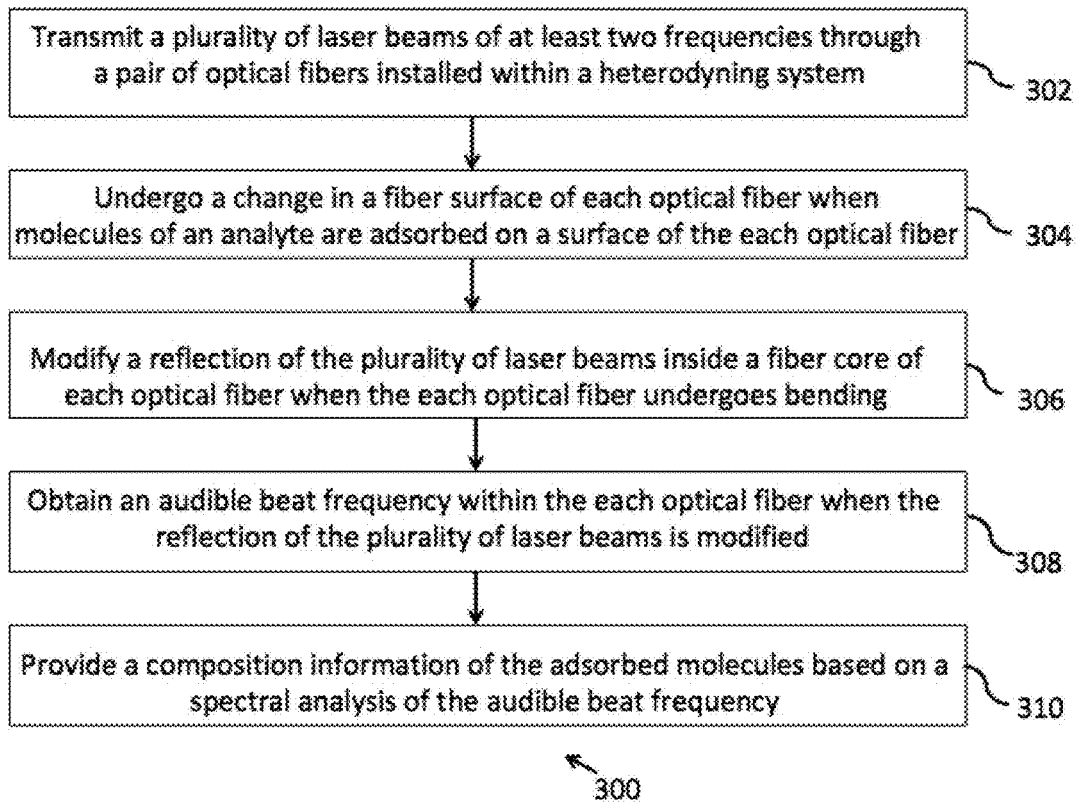
FIG. 3 is a flowchart illustrating a method for cancer biomarker detection, according to one of the preferred embodiment of the present invention.

FIG. 3 is a flowchart 300 depicting a method for cancer biomarker detection, according to an embodiment of the present invention.

At 302, a plurality of laser beams of at least two frequencies is transmitted through a pair of optical fibers installed within a heterodyning system. In an embodiment, the plurality of laser beams is generated by a tunable laser source. The plurality of laser beams is passed through a beam expander, that increases a size of the laser beams, before transmitting it through a pair of optical fibers.

At 304, a change in a fiber surface of each optical fiber occurs when molecules of an analyte are adsorbed on a surface of the each optical fiber. Due to molecular conformational structure micro bending of the each optical fiber occurs, that results in changing a pattern of reflection of the plurality of laser beams that pass through the each optical fiber.

At 306, a reflection of the plurality of laser beams within each optical fiber is modified when each optical fiber undergoes bending.

At 308, an audible beat frequency is obtained within the each optical fiber when the reflection of the plurality of laser beams is modified. The beat frequency may be detected by a pair of phototransistors, each phototransistor connected to an optical fiber output. The pair of phototransistors provide an electrical equivalent output voltage. The output voltage can be rectified and amplified by an operational amplifier to produce an output voltage that is provided to a frequency spectrum analyzer and an audio speaker.

At 310, a composition information of the adsorbed molecules is provided by a frequency spectrum analyzer based on a spectral analysis of the audible beat frequency. For example, based on the composition information of the adsorbed molecules, cancer biomarkers may be detected thereby facilitating early detection of cancer. Further, the audio speaker may provide a sound output of the output voltage.

It is to be understood that the above description is intended to be illustrative, and not restrictive. For example, the above-discussed embodiments may be used in combination with each other. Many other embodiments will be apparent to those of skill in the art upon reviewing the above description.

The benefits and advantages which may be provided by the present invention have been described above with regard to specific embodiments. These benefits and advantages, and any elements or limitations that may cause them to occur or to become more pronounced are not to be construed as critical, required, or essential features of any or all of the embodiments.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention.

What is claimed:
1. A method comprising:
 transmitting a plurality of laser beams of at least two frequencies through a pair of optical fibers installed within a heterodyning system;
 undergoing a change in a fiber surface of each optical fiber when molecules of an analyte are adsorbed on a surface of the each optical fiber;

modifying a reflection of the plurality of laser beams inside a fiber core of each optical fiber when each optical fiber undergoes bending;

obtaining, by the pair of optical fibers, an audible beat frequency within each optical fiber when the reflection of the plurality of laser beams is modified; and providing, by a frequency spectrum analyzer, a composition information of the adsorbed molecules based on a spectral analysis of the audible beat frequency.

2. The method of claim 1, further comprising:
producing, by a tunable laser, the plurality of laser beams;
receiving, by a beam expander, the plurality of laser beams from the tunable laser; and increasing, by the beam expander, a size of each of the plurality of laser beams.

3. The method of claim 1, further comprising:
detecting, by a pair of phototransistors, the audible beat frequency; and
producing, by the pair of phototransistors, an electric current output equivalent to the beat frequency.

4. The method of claim 3, further comprising:
receiving, by a pair of RC circuits, the equivalent electric current output; and
producing, by the pair of RC circuits, a rectified output voltage.

5. The method of claim 4, further comprising:
receiving, by a pair of potentiometers, the rectified output voltage from the pair of RC circuits;
producing, by the pair of potentiometers, a scaled output voltage of the rectified output voltage;
providing, by the pair of potentiometers, the scaled output voltage as input to an operational amplifier; and
producing, by the operational amplifier, an output voltage equivalent to a gained difference between the scaled output voltage.

6. The method of claim 4, further comprising:
receiving, by a capacitor, as input the output voltage from the operational amplifier; and
output, by an audio speaker, a sound recording of the output voltage.

7. The method of claim 1, further comprising:
detecting, by a pair of bifurcated optical fibers, fluorescence of the adsorbed molecules;
delivering, the fluorescence to a ultraviolet and visible (UV-Vis) spectrometer; and
monitoring, by a cadmium-sulfide (CdS) sensor, a dynamic change in the plurality of laser beams transmitted through the pair of optical fibers.

8. The method of claim 1, wherein the analyte is present in a biological sample, and wherein the biological sample is blood sample of a human body.

9. The method of claim 1, wherein the molecules is at least one of a cancer biomarker and a protein.

* * * * *